United States Patent [19]

Howie et al.

[11] Patent Number: 4,525,289

[45] Date of Patent: Jun. 25, 1985

[54] ALPHA-PHOSPHONO LAURAMIDE LUBRICANT ADDITIVES

[75] Inventors: John K. Howie, Oregonia; Steven S. Bullock, Cincinnati, both of Ohio

[73] Assignee: The Procter & Gamble Company, Cincinnati, Ohio

[21] Appl. No.: 622,354

[22] Filed: Jun. 19, 1984

Related U.S. Application Data

[63] Continuation of Ser. No. 529,899, Sep. 6, 1983, abandoned, which is a continuation of Ser. No. 335,315, Dec. 29, 1981, abandoned.

[51] Int. Cl.$^3$ .............................................. C10M 1/46
[52] U.S. Cl. .................................... 252/49.9; 260/943
[58] Field of Search ......... 252/49.9; 260/943, 502.5 R

[56] References Cited

U.S. PATENT DOCUMENTS

| | | | |
|---|---|---|---|
| 2,185,541 | 1/1940 | Cahn | 200/400 |
| 2,363,510 | 11/1944 | Farrington et al. | 252/39 |
| 2,373,627 | 4/1945 | Dietrich | 252/49.9 X |
| 2,494,283 | 1/1950 | Cassaday et al. | 252/49.9 X |
| 2,706,194 | 4/1955 | Morris et al. | 252/49.9 X |
| 2,847,442 | 8/1958 | Sallmann | 252/49.9 X |
| 2,963,458 | 12/1960 | Swern | 260/30.6 |
| 2,973,380 | 2/1961 | Swern | 260/403 |
| 3,066,140 | 11/1962 | Speziale | 260/247.7 |
| 3,778,375 | 12/1973 | Braid | 252/49.9 |
| 3,830,885 | 8/1974 | Petersen | 260/943 |
| 3,849,321 | 11/1974 | Magne et al. | 252/46.7 |
| 3,911,120 | 10/1975 | Mod et al. | 260/943 X |
| 4,044,075 | 8/1977 | Jäger | 260/943 |
| 4,138,432 | 2/1979 | Von Esch | 260/943 X |

OTHER PUBLICATIONS

Hsu, S. M., "Antiwear and Lubricity Additives for Lubricants", NBS Spec. Publ., 1977, pp. 172–185.

Rounds, Fred G., "Additive Interactions and Their Effect on the Performance of a Zinc Dialkyl Dithiophosphate", Asle, 1976.

Smalheer, C. V., et al., "Lubricant Additives", 1967, pp. 1–11.

*Primary Examiner*—Andrew H. Metz
*Attorney, Agent, or Firm*—Steven J. Goldstein; Edmund F. Gebhardt; Richard C. Witte

[57] ABSTRACT

Alpha-phosphono amides useful as antiwear and friction-reducing additives for lubricants and liquid hydrocarbon fuels are disclosed. The compounds are non-corrosive and effective at relatively low concentrations when compared with common phosphorus-based additives.

15 Claims, No Drawings

ALPHA-PHOSPHONO LAURAMIDE LUBRICANT ADDITIVES

This is a continuation of application Ser. No. 529,899, filed Sept. 6, 1983, which is a continuation of Ser. No. 335,315, Dec. 29, 1981, both abandoned.

TECHNICAL FIELD

The present invention relates to alpha-phosphono amide compounds which are useful as antiwear and friction-reducing additives for lubricant compositions and liquid hydrocarbon fuels. The compounds are non-corrosive and effective at relatively low concentrations when compared with common phosphorus-based antiwear and friction-reducing additives.

BACKGROUND ART

U.S. Pat. No. 2,973,380, Swern, issued Feb. 28, 1961, discloses alpha-phosphono acid ester plasticizer compounds. In the form of partially hydrolyzed alpha-dialkylphosphono carboxylic acids, the compounds are said to be useful in making lubricant greases.

U.S. Pat. No. 2,185,541, Cahn, issued Jan. 2, 1940, describes a wide variety of alpha-substituted carboxylic acids as interface modifying agents. The hydrophilic group at the alpha position generally is an oxygenated sulfur or phosphorus group, and can be phosphonic acid. The patent also states that the carboxyl group of the acid can be esterified or converted to an amide.

U.S. Pat. No. 2,363,510, Farrington et al., issued Nov. 28, 1944, discloses alpha-, beta- and gamma-substituted carboxylate salts as non-corrosive detergent additives for lubricants. The substituents must contain either nitrogen, phosphorus, arsenic, antimony or bismuth, and can be phospho and phosphonato groups.

U.S. Pat. No. 3,830,885, Petersen, issued Aug. 20, 1974, discloses certain dialkyl carbamylphosphonates useful as intermediates in the preparation of dialkyl N,N-dialkoxymethyl carbamylphosphonate flameproofing additives.

German Pat. No. 27 56 488, Schmidt et al., published June 29, 1978, discloses dithiophosphato acid and amide compounds which are said to be useful as non-corrosive extreme pressure additives for lubricants.

Zinc dialkyl dithiophosphates are commonly used in lubricants as antiwear additives and antioxidants. However, since these compounds do not reduce friction between moving surfaces, and can even increase friction under certain conditions, lubricants containing them often also require special additives to minimize energy losses due to friction. In order to reduce friction and thereby improve fuel efficiency, crankcase lubricants have recently been prepared using low-viscosity base oils. However, current antiwear additives do not provide adequate wear protection in such low-viscosity oils. New antiwear additives which provide lower phosphorus levels than the zinc dialkyl dithiophosphates are also needed for crankcase lubricants in order to reduce phosphorus poisoning of catalytic converters and other emission control equipment. Finally, more effective additives for liquid hydrocarbon fuels are needed to reduce wear and friction in fuel pumps and the upper cylinders of internal combustion engines.

While some alpha-phosphono carboxylic acids and esters known in the art could provide antiwear and friction-reducing benefits in lubricants and fuels, it has been found that they are generally too corrosive to be used in such compositions. Thus, there is a continuing need for the development of improved antiwear and friction-reducing additives for lubricants and fuels.

SUMMARY OF THE INVENTION

The present invention encompasses compounds of the formula

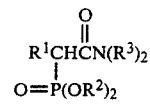

wherein $R^1$ is a $C_6$–$C_{20}$ hydrocarbyl group; each $R^2$ is hydrogen or a $C_1$–$C_{12}$ hydrocarbyl group; each $R^3$ is hydrogen or a $C_1$–$C_{12}$ hydrocarbyl group, or the $R^3$ substituents are joined to form a $C_4$–$C_6$ heteroring with the nitrogen atom; provided that the total number of carbon atoms in the $R^1$, $R^2$ and $R^3$ substituents is from about 10 to about 36.

The invention also encompasses lubricant compositions, liquid hydrocarbon fuels, and additive compositions therefor, containing the above compounds.

DETAILED DESCRIPTION OF THE INVENTION

The alpha-phosphono amides of the present invention are useful as antiwear and friction-reducing additives for lubricant compositions and liquid hydrocarbon fuels. The compounds are non-corrosive when compared with corresponding alpha-phosphono acids and esters, and effective at relatively low concentrations when compared with other phosphorus-based additives, such as the zinc dialkyl dithiophosphonates. Thus, the compounds can provide lower levels of phosphorus in crankcase lubricants and fuels, and thereby reduce phosphorus poisoning of catalytic converters and other emission control equipment.

While not intending to be limited by theory, it is believed that the highly polar nature of the present compounds causes them to more readily adsorb at metal surfaces than do compounds such as the zinc dialkyl dithiophosphates. Since the present compounds provide low coefficients of friction between moving surfaces, they function as effective friction-reducing agents. It is also believed that mechanical and thermal energy can break the bond between the alpha-carbon atom and the phosphorus atom of the present compounds, freeing some of the phosphorus to chemically react with metal surfaces and form a stable antiwear film. Thus, the present compounds can provide both antiwear and friction-reducing benefits in lubricants and fuels, depending upon the degree to which chemical reactions take place with metal surfaces. The compounds are also thought to provide some detergency, corrosion inhibition and metal deactivation benefits when added to lubricants and fuels.

In the general formula for the compounds herein, $R^1$ can be any $C_6$–$C_{20}$ hydrocarbyl group. (As used herein, "hydrocarbyl" is intended to include straight and branched chain alkyl, alkenyl, alkynyl, cycloalkyl, cycloalkenyl, aryl, arylalkyl, alkylaryl and the like groups. It also includes substituted hydrocarbyl groups in which the substituent can be, for example, a chloro, fluoro, bromo, nitro, ethoxy, polyethoxy, propoxy, hydroxy, pentylthio or mercapto group.) Highly preferred compounds herein are those in which $R^1$ is a $C_8$–$C_{16}$ alkyl group.

Each $R^2$ substituent in the general formula for the present compounds can be hydrogen or a $C_1$–$C_{12}$ hydrocarbyl group, but preferably is a $C_1$–$C_8$ hydrocarbyl group.

Each $R^3$ in the general formula for the present compounds can be hydrogen or a $C_1$–$C_{12}$ hydrocarbyl group. The $R^3$ substituents can also be joined to form a $C_4$–$C_6$ heteroring with the nitrogen atom, such as an azetidine, pyrrolidine, piperidine or morpholine ring. Highly preferred compounds herein are those in which each $R^3$ is hydrogen. These primary amides generally provide greatest antiwear and friction-reducing benefits.

It will be appreciated that the above substituents should be selected such that the compounds herein exhibit sufficient solubility for their intended use. Thus, the total number of carbon atoms in the $R^1$ and $R^2$ and $R^3$ substituents should be from about 10 to about 36, preferably from about 12 to about 24.

A particularly preferred compound herein is alpha-(diisopropyl phosphono)lauramide (i.e., in the general formula, $R^1$ is a $C_{10}$ alkyl group, each $R^2$ is an isopropyl group and each $R^3$ is hydrogen). Examples of other preferred primary amides are alpha-(diisopropyl phosphono)stearamide, alpha-(dimethyl phosphono)lauramide, the alpha-(dimethyl phosphono)amide of tallow fatty acid, the alpha-(diisopropyl phophono)amide of coconut fatty acid, and alpha-(di-2-ethylhexyl phosphono)lauramide. Other compounds useful herein include alpha-phosphonolauramide, alpha-(monomethyl phosphono)stearamide, alpha-(di-2-ethylhexyl phosphono)caprylamide, alpha-(dilauryl phosphono)lauramide, alpha-(methyl ethyl phosphono)oleamide, N,N-dimethyl-alpha-(diisopropyl phosphono)lauramide, N-monomethyl-alpha-(dimethyl phosphono)stearamide, N,N-dioctyl-alpha-(dihydroxyethyl phosphono)caprylamide, N-[alpha-(diisopropyl phosphono)lauroyl]-morpholine, and N-[alpha-(dimethyl phosphono)-stearoyl]piperidine.

The compounds of the present invention can be effectively employed as antiwear and friction-reducing additives in a wide variety of lubricant compositions, including greases obtained therefrom. The compounds are particularly suitable for use in crankcase lubricants prepared for spark-ignited and compression-ignited internal combustion engines, including automobile and truck engines, two-cycle engines, aviation piston engines, marine and low-load diesel engines, and the like. The compounds are also useful as antiwear and friction-reducing additives for automatic transmission fluids, turbine lubricating oils, hydraulic fluids, and similar lubricating oils and greases prepared therefrom. The present compounds can also be used as friction-reducing additives for compositions such as gear oils, metalworking lubricants, cutting oils and transaxle lubricants. However, because such compositions encounter more heavily-loaded conditions, they generally should also contain sulfur-based extreme pressure additives to prevent scuffing. Compounds of the present invention in which one or both of the $R^2$ substituents is hydrogen are more chemically active and are therefore preferred for use in such compositions.

Lubricant compositions herein can be prepared by a variety of methods known in the art. Typically, a concentrated solution or substantially stable suspension of the present compounds will be prepared for addition to a base lubricating oil or to an otherwise fully formulated lubricant composition. Such a concentrated lubricant additive composition can comprise from about 5% to about 90%, preferably from about 20% to about 60%, by weight of the compounds herein and from about 10% to about 95%, preferably from about 30% to about 70%, by weight of a lubricant additive carrier material. The carrier material can be selected from any of the substantially inert liquid hydrocarbon solvents and diluents known in the art, including the natural and synthetic base lubricating oils hereinafter described, kerosene, xylene, benzene and mixtures thereof. The carrier is preferably a mineral or synthetic oil, or mixtures thereof.

Lubricant additive compositions herein can also contain from about 5% to about 80%, preferably from about 20% to about 60%, by weight of other additives typically found in lubricants. Such additives include ashless dispersants, detergents, oxidation inhibitors, corrosion inhibitors, extreme pressure agents, rust inhibitors, pour point depressants, viscosity index improvers, foam inhibitors, supplemental antiwear and friction-reducing agents, and mixtures thereof. These optional additives are more fully described in U.S. Pat. No. 4,199,463, Ryer et al., issued Apr. 22, 1980, particularly from column 10, line 16 through column 11, line 37, incorporated herein by reference.

Fully formulated lubricant compositions herein comprise from about 0.01% to about 10%, preferably from about 0.1% to about 2%, by weight of the present compounds and a major amount, preferably from about 70% to about 95% by weight, of a base lubricating oil. The base oil can be derived from either natural or synthetic sources. Suitable natural oils include animal oils, such as lard oil; vegetable oils, such as castor oil; and mineral oils, such as solvent-treated or acid-treated mineral oils of the paraffinic, naphthenic, and mixed paraffinic-naphthenic types. Oils of lubricating viscosity derived from coal or shale are also useful herein. The mineral lubricating oils are usually preferred because of their availability and low cost.

Synthetic base lubricating oils are also preferred for use in the present compositions. Synthetic oils are described in U.S. Pat. No. 4,208,357, Hoke, issued June 17, 1980, particularly from column 9, line 52 to column 10, line 37, incorporated herein by reference, and are generally synthetic hydrocarbon oils, polyalkylene oxide oils, polyacetal oils, polysilicone oils or synthetic ester oils.

Preferred synthetic oils for use herein include the alkylbenzenes and liquid polymers of alpha-olefins, having a viscosity of less than about 80 SUS at 100° C. Particularly preferred are the hydrogenated liquid oligomers of $C_6$–$C_{12}$ alpha-olefins, such as alpha-decene trimer and tetramer. Other preferred synthetic oils are the esters made from monohydric alcohols and polycarboxylic acids, such as didodecyl adipate, di-(2-ethylhexyl)adipate, dilauryl sebacate, and the esters made from polyhydric alcohols and monocarboxylic acids, such as trimethylol propane tripelargonate and pentaerythritol tetracaproate. Particularly preferred are the pentaerythritol, neopentyl glycol and trimethylol propane esters of $C_7$–$C_9$ acids. Blends of mineral and synthetic oils, such as those containing about 5–25% by weight of hydrogenated alpha-decene trimer or of di-(2-ethylhexyl)adipate and about 75–95% by weight of 150 SUS (38° C.) mineral oil, are also useful herein, especially for preparing low viscosity motor oils (e.g. SAE 5W 20).

Fully formulated lubricant compositions herein preferably also contain from about 0.01% to about 30%, more preferably from about 1% to about 20%, by weight of other additives typically found in lubricants, such as those described above for use in lubricant additive compositions.

Preferred crankcase lubricants herein comprise from about 80% to about 95% by weight of a mineral or synthetic base oil, or mixtures thereof, from about 5% to about 20% by weight of the above conventional additives, and from about 0.1% to about 2% by weight of the present compounds.

The compounds of the present invention can also be used as antiwear and friction-reducing additives for a wide variety of liquid hydrocarbon fuels, including gasoline, alcohols, especially methanol, ethanol and mixtures thereof with gasoline, oxygenated octane improvers, synthetic fuels derived from coal or shale, kerosene, diesel fuels, No. 2 fuel oil and other middle distillates characterized by boiling within the range of about 120° C. to 500° C.

Concentrated fuel additive compositions herein comprise from about 0.5% to about 90%, preferably from about 20% to about 60%, by weight of the present compounds, and from about 10% to about 99.5%, preferably from about 30% to about 70%, by weight of a fuel additive carrier material. The carrier material can be selected from any of the liquid hydrocarbon fuels herein, as well as any of the substantially inert liquid hydrocarbon solvents and diluents known in the art, such as natural and synthetic base lubricating oils, kerosene, xylene, benzene and mixtures thereof. In addition, such fuel additive compositions can contain from about 5% to about 80%, preferably from about 20% to about 60%, by weight of other conventional additives. These include dyes, antioxidants, detergents, preignition/antiknock additives, anti-icing additives for gasoline, pour point depressants and cold flow improvers for the middle distillate fuels, and supplemental antiwear and friction-reducing additives.

Fully formulated fuels herein comprise from about 0.0001% to about 0.5%, preferably from about 0.001% to about 0.1%, by weight of the present compounds and a major amount, preferably at least about 98% by weight, of the fuel. Such compositions will also generally contain minor amounts, e.g., less than about 2% by weight, of the above conventional fuel additives.

The following non-limiting examples illustrate the compounds and compositions of the present invention.

All percentages, parts, and ratios used herein are by weight unless otherwise specified.

EXAMPLE I

A preferred compound of the present invention, alpha-(diisopropyl phosphono)lauramide, was prepared as follows.

Step 1: Preparation of diisopropyl undecylphosphonate:

69 g (3 moles) of sodium and 500 ml of freshly distilled tetrahydrofuran (THF) were added to a flame-dried, 5 liter flask fitted with mechanical stirrer, condenser, thermometer and addition funnel. 664 g (4 moles) of diisopropyl phosphite was added in 500 ml of THF. The reaction was initially heated but became sufficiently exothermic to reflux the THF. Some supplemental heating was required to maintain reflux until all the sodium was consumed (total reaction time of about 6 hours). The mixture was cooled to 60° C. and held there while 478.4 g (2 moles) of 1-bromoundecane was added in 500 ml of THF. After stirring overnight at 60° C., sodium bromide formed as a precipitate and was filtered off. 200 ml of distilled water was added to the filtrate to react with excess sodium diisopropyl phosphite. Concentrated hydrochloric acid (HCl) was then added to lower the pH to 2.0. The solution was extracted with one liter of ether three times. The ether layers were washed twice with water, dried over magnesium sulfate, filtered and flash evaporated. The crude product was heated in a Kugelrohr distillation apparatus to 110° C. at 0.03 mm until no diisopropyl phosphite distilled over. The residual product weighed 598 g (93.3% yield) and was sufficiently pure (by $^1$H NMR) for use in the next step.

Step 2: Preparation of alpha-(diisopropyl phosphono)-lauric acid:

196 g (1.94 moles) of diisopropylamine was added to a flame-dried, 5 liter flask fitted with mechanical stirrer, condenser, thermometer and addition funnel. The flask was cooled to 0°–10° C. using a dry ice/acetone bath. 808 ml of n-butyllithium (2.4M, 1.95 moles) was slowly added, while the flask was kept at 0°–10° C. The solution was stirred for an additional 15 minutes and then chilled to −78° C. 598 g (1.84 moles) of diisopropyl undecylphosphonate was added in 1000 ml of freshly distilled THF. (The addition rate should be slow enough to maintain the temperature below −60° C.) The mixture was stirred for an additional 2 hours and then poured carefully into a 12 liter flask containing about 2 kg of dry ice in 3.78 liters of ether. This mixture was allowed to stand and warm slowly overnight. The solution was extracted with water to collect the lithium salt of the product. The organic layers contained any unreacted diisopropyl undecylphosphonate. The water layer was acidified to pH 2.0 using concentrated HCl and extracted with 500 ml of ether three times. The combined ether extracts were dried over magnesium sulfate, filtered, and flash evaporated. The product was a viscous oil weighing 553 g (81% yield) and was sufficiently pure (by $^1$H NMR) for use in the next step.

Step 3: Preparation of alpha-(diisopropyl phosphono)-lauramide:

553 g (1.57 moles) of alpha-(diisopropyl phosphono)-lauric acid was placed in a 3 liter flask. 791 g (6.28 moles) of distilled oxalyl chloride was carefully added while maintaining the temperature at or slightly below 35° C. (Temperatures much above 35° C. result in oxalyl chloride attack on the phosphonate esters, and too rapid addition results in foaming.) The temperature was maintained at 35° C. for 4 hours, after which I.R. analysis revealed all the acid had converted to the acid chloride. Excess oxalyl chloride was distilled off while maintaining the temperature at 35° C. or below. The product was then diluted with an equal volume of freshly distilled THF and added to a 3 liter flask containing about 1 liter of condensed ammonia. Following a vigorous reaction, the mixture was allowed to stand and warm overnight. Excess ammonia was driven off using a steam bath, and 1 liter of chloroform was added and heated to reflux. The hot chloroform solution was filtered to remove insoluble ammonium chloride and then flash evaporated. The solid residue was dissolved as a 30% solution in pentane, chilled to −78° C. and then placed in a refrigerator. After standing overnight, a crystalline product was collected, dried and ground to a powder. The product weighed 417 g (70% yield) and was pure as verified by TLC and $^1$H NMR.

The alpha-(diisopropyl phosphono)lauric acid of Step 2 was also prepared as follows.

6.9 g (0.3 mole) of sodium and 300 ml of toluene were added to a flame-dried, 1 liter flask fitted with a mechanical stirrer, condenser, thermometer and addition funnel. 66.5 g (0.4 mole) of diisopropyl phosphite was added and the mixture refluxed for 4 hours until all the sodium was consumed. 5 g (0.02 mole) of alpha-chlorolauric acid was added in 100 ml of toluene and the refluxing continued for 24 hours, at which time a light precipitate was evident. The flask was cooled and distilled water was added to react with excess sodium phosphite. The pH was adjusted to 2.0 with concentrated HCl. The mixture was then extracted with ether, dried over magnesium sulfate, filtered and flash evaporated. The product (90% yield) was isopropyl alpha-(diisopropyl phosphono)laurate, as shown by $^{13}C$ NMR. It could readily be hydrolyzed to the corresponding free acid in base at room temperature.

The alpha-chlorolauric acid used in the above procedure can be obtained by the process disclosed in U.S. Pat. No. 4,148,811, Crawford, issued Apr. 10, 1979, incorporated herein by reference. A preferred process for preparing 1,4-bis(dicyanomethylene)cyclohexane, the precursor of the tetracyanoquinodimethane (TCNQ) used in the process, is disclosed in U.S. Pat. No. 4,229,364, Crawford, issued Oct. 21, 1980, incorporated herein by reference. Other compounds herein can be obtained when the alpha-chlorolauric acid is replaced with other alpha-chloro acids derived from, for example, caprylic acid, capric acid, myristic acid, palmitic acid, stearic acid, oleic acid, eicosanoic acid, mixed coconut oil fatty acids, mixed palm oil fatty acids, mixed lard fatty acids, mixed soybean oil fatty acids, and mixed tallow fatty acids.

Other compounds of the present invention can be prepared by the above procedure by replacing the ammonia in Step 3 with morpholine, piperidine, pyrrolidine, methylamine, dimethylamine and a variety of other primary and secondary amines.

EXAMPLE II

Crankcase lubricants of the present invention are as follows:

| Component | Wt. % | | | | |
|---|---|---|---|---|---|
| | A | B | C | D | E |
| SAE 30 mineral oil | 91.5 | 89.0 | | | |
| 100 N mineral oil | | | 58.4 | | |
| 150 N mineral oil | | | | 87.05 | |
| Alpha-decene trimer | | | 25.0 | | 70.88 |
| Pentaerythritol ester of mixed $C_7$–$C_9$ acids | | | | | 17.72 |
| Overbased calcium sulfonate (TBN 300) | 2.0 | 1.2 | 1.2 | 0.6 | |
| Overbased magnesium sulfonate (TBN 400) | | 0.8 | 0.8 | 0.4 | |
| Calcium phenate (TBN 240) | | | | | 1.0 |
| N—substituted polyisobutenyl succinimide dispersant | 3.0 | 5.0 | 5.0 | 3.0 | 3.0 |
| 4,4′methylenebis-(2,6-di-t-butylphenol) | 1.0 | 1.0 | 1.5 | 1.5 | 1.0 |
| Alkylated diphenylamine antioxidant | | 2.0 | 1.5 | 1.5 | |
| Zinc diamyldithiocarbamate antioxidant | 2.0 | | | | 1.0 |
| Polymethyacrylate viscosity index improver | | 6.5 | 5.2 | 4.5 | |
| Dimethylpolysiloxane foam inhibitor | 0.001 | 0.001 | 0.001 | 0.001 | 0.001 |
| Alpha-(dimethyl phosphono) amine of tallow fatty acid | 0.5 | | | | |
| Alpha-(diisopropyl phosphono) lauramide | | 1.0 | 0.3 | 0.75 | 0.3 |
| Alpha-(di-2-ethylhexyl phosphono) lauramide | | | 0.3 | | 0.6 |

The above compositions are prepared by heating the mineral or synthetic base oils to about 60°–65° C. and maintaining the temperature under a nitrogen blanket. The viscosity index improvers (if used) are added and mixed with the base oils. The alpha-phosphono amide compounds are then added and the compositions mixed for 1 hour. The antioxidants, dispersants, detergents and foam inhibitors are then separately added, with mixing for one-half hour between additions of the components.

The above compositions can also be prepared by adding concentrated solutions containing about 30% by weight of the alpha-phosphono amide compounds and about 70% by weight of the indicated mineral or synthetic oils to otherwise fully formulated crankcase lubricants containing the components, except for the alpha-phosphono amides. The above compositions can also conveniently be prepared by adding concentrated solutions containing about 50% by weight of the additives and about 50% by weight of the mineral or synthetic oils, to base oils which are the mineral or synthetic oils.

EXAMPLE III

An automatic transmission fluid of the present invention is as follows:

| Component | Wt. % |
|---|---|
| 100 N mineral oil | 83.88 |
| 200 N mineral oil | 9.32 |
| N—substituted polyisobutenyl succinimide dispersant | 3.5 |
| Zinc diamyldithiocarbamate antioxidant | 0.5 |
| Dimethylpolysiloxane foam inhibitor | 0.001 |
| Polymethylacrylate viscosity index improver | 2.0 |
| Alpha-(diethyl phosphono)stearamide | 0.8 |

EXAMPLE IV

A marine diesel engine oil is as follows:

| Component | Wt. % |
|---|---|
| 200 N mineral oil | 88.0 |
| Overbased calcium sulfonate (TBN 300) | 5.0 |
| N—substituted polyisobutenyl succinimide dispersant | 5.0 |
| Dimethylpolysiloxane foam inhibitor | 0.001 |
| 4,4′methylenebis(2,6-di-t-butylphenol) | 1.0 |
| Alpha-(diisopropyl phosphono)myristamide | 1.0 |

EXAMPLE V

A 2-cycle engine oil is as follows:

| Component | Wt. % |
|---|---|
| SAE 30 mineral oil | 96.8 |

-continued

| Component | Wt. % |
|---|---|
| Overbased calcium sulfonate (TBN 300) | 1.5 |
| N—substituted polyisobutenyl succinimide dispersant | 1.5 |
| Isopropanol, $C_8$–$C_{10}$ alcohol coupling agents | 0.1 |
| Alpha-(dimethyl phosphono)amide of coconut fatty acid | 0.1 |

EXAMPLE VI

A lubricating grease of the present invention is as follows:

| Component | Wt. % |
|---|---|
| SAE 20 mineral oil | 93.5 |
| Calcium tallow fatty acid soap | 10.0 |
| Overbased calcium sulfonate (TBN 300) | 1.5 |
| Normal calcium sulfonate (TBN 30) | 1.0 |
| Sulfurized olefin E.P. additive | 3.5 |
| Alkylated diphenylamine antioxidant | 0.5 |
| Alpha-(di-n-butyl phosphono)stearamide | 0.75 |

EXAMPLE VII

An aircraft gas turbine oil is as follows:

| Component | Wt. % |
|---|---|
| Trimethylol propane ester of mixed $C_7$–$C_9$ acids | 96.5 |
| Alkylated diphenylamine antioxidant | 1.0 |
| Polymethacrylate viscosity index improver | 1.0 |
| Alkyl bisulfite hydrolytic stabilizer | 0.25 |
| Zinc diamyldithiocarbamate metal deactivator | 0.25 |
| Alpha-(diphenyl phosphono)lauramide | 1.0 |

EXAMPLE VIII

A gear oil is as follows:

| Component | Wt. % |
|---|---|
| SAE 90 mineral oil | 95.25 |
| Sulfurized olefin E.P. additive | 4.0 |
| Ethylenediamine dinonylnapththene sulfonate | 0.5 |
| Alpha-(monomethyl phosphono)lauramide | 0.25 |

EXAMPLE IX

A cutting oil herein is as follows:

| Component | Wt. % |
|---|---|
| 200 N mineral oil | 91.75 |
| Sulfurized olefin E.P. additive | 8.0 |
| 4,4'methylenebis(2,6-di-t-butylphenol) | 0.25 |
| Alpha-phosphonolauramide | 1.0 |

EXAMPLE X

A concentrated fuel additive composition herein contains about 25% by weight of alpha-(diisopropyl phosphono)lauramide and about 75% by weight of diesel fuel. It can be added to a fully formulated diesel fuel, at a level providing about 0.05% by weight of the alpha-phosphono amide, to reduce wear and friction in internal combustion engines.

Other compositions herein can be obtained by adding about 0.001% by weight of the alpha-(diisopropyl phosphono)amide of tallow fatty acid to gasoline or mixtures thereof with ethanol or methanol.

What is claimed is:

1. A compound of the formula

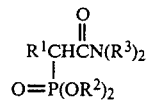

wherein $R^1$ is a $C_{10}$ hydrocarbyl group; each $R^2$ is hydrogen or a $C_1$–$C_{12}$ hydrocarbyl group; each $R^3$ is hydrogen or a $C_1$–$C_{12}$ hydrocarbyl group, or the $R^3$ substituents are joined to form a $C_4$–$C_6$ heteroring with the nitrogen atom; provided that the total number of carbon atoms in the $R^1$, $R^2$ and $R^3$ substituents is from about 10 to about 36.

2. A compound according to claim 1 wherein the total number of carbon atoms in the $R^1$, $R^2$ and $R^3$ substituents is from about 12 to about 24.

3. A compound according to claim 1 wherein each $R^2$ is a $C_1$–$C_8$ alkyl group.

4. A compound according to claim 1 wherein each $R^3$ is hydrogen.

5. A compound according to claim 4 wherein each $R^2$ is a $C_1$–$C_8$ alkyl group.

6. A compound according to claim 5 wherein $R^1$ is a $C_{10}$ alkyl group and each $R^2$ is an isopropyl group.

7. A lubricant additive composition comprising from about 10% to about 95% by weight of a lubricant additive carrier material and from about 5% to about 90% by weight of a compound of the formula

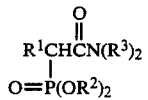

wherein $R^1$ is a $C_{10}$ hydrocarbyl group; each $R^2$ is hydrogen or a $C_1$–$C_{12}$ hydrocarbyl group; each $R^3$ is hydrogen or a $C_1$–$C_{12}$ hydrocarbyl group, or the $R^3$ substituents are joined to form a $C_4$–$C_6$ heteroring with the nitrogen atom; provided that the total number of carbon atoms in the $R^1$, $R^2$ and $R^3$ substituents is from about 10 to about 36.

8. A lubricant composition comprising a major amount of a base lubricating oil and from about 0.01% to about 2% by weight of a compound of the formula

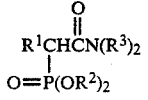

wherein $R^1$ is a $C_{10}$ hydrocarbyl group; each $R^2$ is hydrogen or a $C_1$–$C_{12}$ hydrocarbyl group; each $R^3$ is hydrogen or a $C_1$–$C_{12}$ hydrocarbyl group, or the $R^3$ substituents are joined to form a $C_4$–$C_6$ heteroring with the nitrogen atom; provided that the total number of carbon atoms in the $R^1$, $R^2$ and $R^3$ substituents is from about 10 to about 36.

9. In a lubricant additive composition comprising from about 10% to about 95% by weight of a lubricant additive carrier material and from about 5% to about 80% by weight of a conventional lubricant additive, the improvement comprising the presence in the composition of from about 5% to about 90% by weight of a compound of the formula

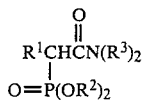

wherein $R^1$ is a $C_{10}$ hydrocarbyl group; each $R^2$ is hydrogen or a $C_1$-$C_{12}$ hydrocarbyl group; each $R^3$ is hydrogen or a $C_1$-$C_{12}$ hydrocarbyl group, or the $R^3$ substituents are joined to form a $C_4$-$C_6$ heteroring with the nitrogen atom; provided that the total number of carbon atoms in the $R^1$, $R^2$ and $R^3$ substituents is from about 10 to about 36.

10. A lubricant additive composition according to claim 9 wherein the carrier mixture is a mineral or synthetic oil, or mixtures thereof.

11. A lubricant additive composition according to claim 10 wherein $R^1$ is a $C_8$-$C_{16}$ alkyl group, each $R^2$ is a $C_1$-$C_8$ alkyl group and each $R^3$ is hydrogen.

12. In a lubricant composition comprising a major amount of a base lubricating oil and from about 0.01% to about 30% by weight of a conventional lubricant additive, the improvement comprising the presence in the composition of from about 0.01% to about 10% by weight of a compound of the formula

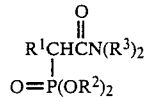

wherein $R^1$ is a $C_{10}$ hydrocarbyl group; each $R^2$ is hydrogen or a $C_1$-$C_{12}$ hydrocarbyl group; each $R^3$ is hydrogen or a $C_1$-$C_{12}$ hydrocarbyl group, or the $R^3$ substituents are joined to form a $C_4$-$C_6$ heteroring with the nitrogen atom; provided that the total number of carbon atoms in the $R^1$, $R^2$ and $R^3$ substituents is from about 10 to about 36.

13. A lubricant composition according to claim 12 wherein the base lubricating oil is a mineral or synthetic oil, or mixtures thereof.

14. A lubricant composition according to claim 13 wherein each $R^2$ is a $C_1$-$C_8$ alkyl group and each $R^3$ is hydrogen.

15. A crankcase lubricant composition according to claim 14 comprising from about 80% to about 95% by weight of the mineral or synthetic base oil, or mixtures thereof, from about 5% to about 20% by weight of the additive and from about 0.1% to about 2% by weight of the compound.

* * * * *